United States Patent [19]

Warriner

[11] Patent Number: Plant 7,129

[45] Date of Patent: Jan. 30, 1990

[54] ROSE PLANT JACSHINE

[75] Inventor: William A. Warriner, Tustin, Calif.

[73] Assignee: Jackson & Perkins Company, Medford, Oreg.

[21] Appl. No.: 284,135

[22] Filed: Dec. 14, 1988

[51] Int. Cl.[4] ..... A01H 5/00

[52] U.S. Cl. ..... Plt./18

[58] Field of Search ..... Plt./18

*Primary Examiner*—James R. Feyrer

*Attorney, Agent, or Firm*—Majestic, Parsons, Siebert & Hsue

[57] ABSTRACT

A rose variety of the hybrid tea class is provided that has a high production of attractive clear coral pink flowers with disease resistant foliage and vigorous growth.

1 Drawing Sheet

SUMMARY OF THE INVENTION

The present invention relates to a new and distinct variety of rose plant of the hybrid tea class, which was originated by me by crossing an unnamed seedling with the variety Intrigue, U.S. Plant Pat. No. 5,002.

The primary objective of this breeding was to produce a new rose variety of the hybrid tea class with good disease resistance, good plant vigor and well formed coral pink buds and flowers. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. High production (quantity of flowers);
2. Vigorous growth to five feet tall;
3. Coral pink flowers and buds displaying hybrid tea form;
4. Resistance to powdery mildew; and
5. Smooth dark green foliage.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "JACSHINE". Color terminology is in accordance with The Royal Horticultural Society Colour Chart except where an ordinary dictionary significant for the color is apparent.

Observations of the buds and flowers were made from specimens grown in a greenhouse at Somis and Wasco, Calif. in October.

Flower

The blooming habit is continuous. The bud size is one and one-half inches when the petals start to unfurl. The bud form is short and pointed ovoid. The bud color when sepals first divide is near Red Group 37A. When half blown, the upper side of petals is near Red Group 37B. The lower side of petals is near Red Group 37C. The sepals have a color near Yellow-Green Group 147A. The surface texture is slightly rough, having grandular structures on the surface. There are three normally appendaged sepals, and two unappendaged sepals with a hairy edge. The receptacle color is near Yellow Green Group 144A and has a funnel shape, broad size and smooth surface. The peduncle is medium length and has a glandular surface. Peduncle color is light green and the peduncle is stiff and erect. The flower opens slowly in imbricated fashion.

Bloom

Bloom size is medium, with an average open size of three and one-half inches, borne singly, and in clusters that are rounded. The stems are medium in length. The form when first open is high center and retains its form to the end. The outer petals' edges are slightly curled. Under normal conditions there are 25 to 30 petals. The upper side of the petals at the flower center are near Red Group 38B and the reverse side petals at the flower center are near Red Group 38C. The base of petals has a basal spot near Yellow Group 4D. The major color is near Red Group 38B. There are no variegations except for an occasional white stripe on the outer petals. The general tonality at the end of the first day shows no change in color. At the end of the third day, there is still no change in color.

There is slight fragrance. The petal texture is thin. The petal shape is deltoid. The petal form has slightly recurved tips.

The arrangement is imbricated with no petaloids in the center. The blooms drop off cleanly, and last both on the plant and as a cut flower for a long time.

Reproductive Parts

The anthers are of medium size, of yellow color and arranged regularly around the styles. The filaments are yellow, the pollen is gold yellow, the styles are light red, and the stigmas are white.

Plant

The plant has very vigorous, upright growth of bush form.

Foliage

The foliage is medium size and normal in quantity. New foliage is reddish bronze colored and old foliage is near Yellow-Green Group 147A. A normal midstem leave has five leaflets.

The leaflets have an elliptic shape, are smooth textured, and have a serrated edge. The serration is double. The petiole rachis is green, with prickles on the underside. Stipules are medium and serrated. The foliage is resistant to mildew and blackspot under normal growing conditions at Irvine and Wasco, Calif.

Wood

New wood is a reddish color with a smooth bark. Old wood is green with a smooth bark.

Prickles

There are an ordinary number of prickles on the main canes from the base and on the laterals from the main canes. The prickles are medium and hooked downward. The prickles are red colored when young. There are many brown small prickles on the main stalks and laterals.

Parentage

The seed parent was an unnamed seedling. The pollen parent was of the variety Intrigue.

Classification

Botanical is rosa hybrid. Commercial is hybrid tea.

I claim:

1. A new and distinct variety of rose plant of the hybrid tea class substantially as herein shown and described, characterized particularly as to novelty by a clear coral pink flower, disease resistance, smooth dark green foliage, and vigorous growth producing good quantities of flowers.

* * * * *

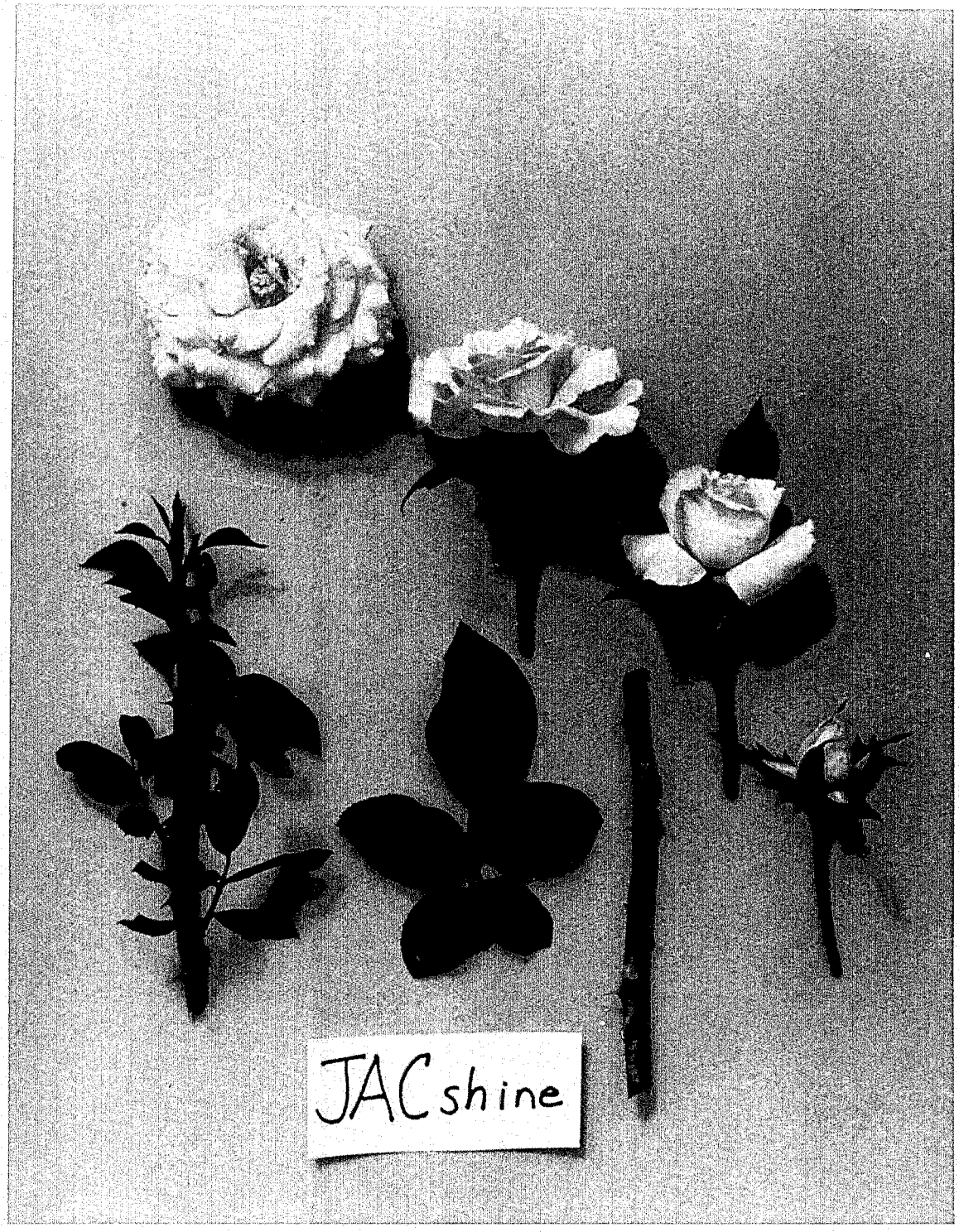
JACshine